United States Patent [19]

Mayer

[11] Patent Number: 5,184,392
[45] Date of Patent: Feb. 9, 1993

[54] OXYGEN SENSOR

[75] Inventor: William N. Mayer, White Bear Lake, Minn.

[73] Assignee: Modern Controls, Inc., Minneapolis, Minn.

[21] Appl. No.: 892,223

[22] Filed: Jun. 2, 1992

Related U.S. Application Data

[62] Division of Ser. No. 731,875, Jul. 18, 1991, Pat. No. 5,139,638.

[51] Int. Cl.⁵ .............................................. H01B 4/00
[52] U.S. Cl. .................................... 29/592.1; 29/825; 204/431; 204/424
[58] Field of Search .................. 204/431; 29/825, 854, 29/868, 872, 592.1, 25.03

[56] References Cited

U.S. PATENT DOCUMENTS 4,085,024  4/1978  Lawson .................... 29/592.1

Primary Examiner—John Niebling
Assistant Examiner—Bruce F. Bell
Attorney, Agent, or Firm—Palmatier, Sjoquist & Helget

[57] ABSTRACT

A method apparatus for constructing an oxygen sensor in a layered construction including an anode element, a cathode element and an intermediate electrolyte-retentive insulator, wherein the layered anode element has a central flat metallic plate with two narrower outer plates bound against respective surfaces of the plate by an electrical conductor wrap, and the cathode element is uniformly compressed toward the anode along an elongate length by elongated support struts.

7 Claims, 3 Drawing Sheets

OXYGEN SENSOR

This specification is a divisional application of Ser. No. 731,875, filed Jul. 18, 1991, now U.S. Pat. No. 5,139,638 issued Aug. 18, 1992.

BACKGROUND OF THE INVENTION

The present invention relates to oxygen sensors, and to a method for making an oxygen sensor, particularly adapted for detecting small quantities of oxygen in a gas flowing through the sensor. The invention is used primarily in connection with instruments for measuring the permeability of films and membranes, wherein oxygen is passed into a chamber, one wall of which is enclosed by a material membrane, and a second chamber on the other side of the membrane is coupled to the sensor. Oxygen which permeates through the membrane is detected by the sensor, which generates an electrical signal proportional to the quantity of oxygen detected.

An oxygen sensor of the type generally related to the present invention is disclosed in U.S. Pat. No. 3,223,597, issued Dec. 14, 1965, to Hersch. The Hersch patent discloses a general construction of an oxygen sensor, and shows the plurality of layers of materials which are or may be utilized to construct a workable sensor. The principles of the Hersch invention are further elaborated upon in a construction disclosed in U.S. Pat. No. 4,085,024, issued Apr. 18, 1978, to Lawson. The Lawson patent discloses a particular construction and method of making the oxygen sensor, utilizing many of the same materials which are the subject of the present invention.

SUMMARY OF THE INVENTION

The present invention is an improved construction, and method of making the construction, which is an advance in the art over the Hersch and Lawson disclosures, which has evolved from the applicant's experience in constructing oxygen sensors. The method of making the oxygen sensor has been improved by manufacturing steps which improve the electrical connections to the anode plate and assure a uniform and continuous surface area contact between the cathode and the anode via the electrolyte-retentive material wrapped around the anode. The size of the anode material is carefully restricted to be smaller than the size of the blade upon which it is mounted to eliminate electrical conductivity problems; the cathode is uniformly compressed over the anode and electrolyte-retentive material by elastomeric bands to assure uniform migration of ions and electrons between the anode and cathode.

It is the principal object of the present invention to provide an oxygen sensor having a construction to assure accurate measurements of oxygen content in gases.

It is another object of the present invention to provide an oxygen sensor having a fast response time to measure oxygen content.

It is another object of the present invention to provide an oxygen sensor having a construction for eliminating electrical conductivity problems between the various active elements of the sensor.

It is another object of the present invention to provide an oxygen sensor having high sensitivity and reliability over an extended period of use.

BRIEF DESCRIPTION OF THE DRAWINGS

The foregoing and other objects and advantages of the present invention will become apparent from the following specification and claims, and with reference to the appended drawings, in which:

DESCRIPTION OF THE PREFERRED EMBODIMENT

Figure 1:
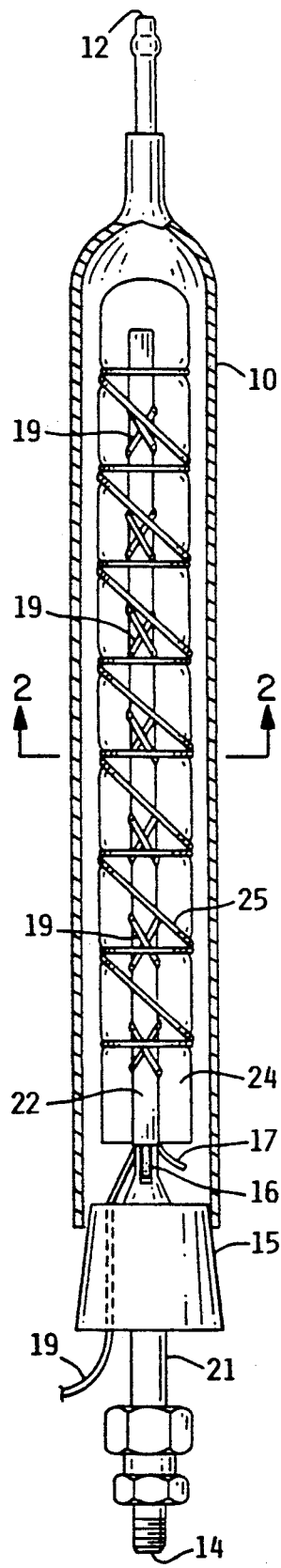
FIG. 1 shows an elevation view in partial cross section of a prior art device.

Referring first to FIG. 1, a prior art oxygen sensor is illustrated, which is constructed in large part according to the principles and techniques illustrated in U.S. Pat. No. 3,223,597, Hersch, and U.S. Pat. No. 4,085,024, Lawson. An oxygen-free envelope 10, preferably constructed of glass, is used to house the active elements of the oxygen sensor. Envelope 10 has an outlet 12 and an inlet 14 to permit the passage of gas therethrough. A rubber stopper 15 provides an effective gas seal at the enlarged open end of envelope 10. The active elements of the oxygen sensor comprise a paddle-shaped blade member 16 which is centrally located within envelope 10. Blade 16 has anode sheet materials 18 and 20 across each facing surface (see FIG. 2), and anode materials 18, 20 are held in close facing contact with blade 16 by means of a criss-cross wrap of wire 17. The anode materials 18, 20 are the same width, or slightly wider, than blade member 16. The respective ends of wire 17 are typically unconnected to any terminus, but are merely cut close to blade 16. The entire combination of blade member 16, anode materials 18, 20, and wire 17 constitute the oxygen sensor anode 23. An insulating material 22 is wrapped over the anode materials, and a second wire 19 is wrapped in criss-cross fashion over insulating material 22. An end of wire 19 is brought to the exterior through the stopper 15 to serve as an active conductor for the oxygen sensor. The metallic inlet tube 21 is affixed to blade member 16 and serves as the second active conductor of the oxygen sensor, and usually is connected to circuit ground. An exterior blanket of carbon felt material 24 is wrapped over the assembly including the insulating material 22, and a nylon thread 25 is wrapped about the entire assembly outside of carbon material 24. In operation, the insulator material is partially saturated with a chemical solution such as potassium hydroxide (KOH), and a test gas is passed through the sensor via inlet 14 and outlet 12. The oxygen content in the gas which flows through the sensor causes a very small current to be generated between the cathode 24 and the anode 23, and this current is collected as a current flow in wire 19 to an external circuit and returned therefrom to metallic tube 21. In order for the operation to be reliable it is important that a good surface contact be maintained between all of the internal components of the device, while at the same time electrically insulating cathode 24 from anode 23.

The present invention is an improvement in the construction of the oxygen sensor to achieve an improved surface contact between the active elements of the device, while at the same time to minimize the possibility of electrical shorting currents arising as a result of construction of the device.

Figure 2:
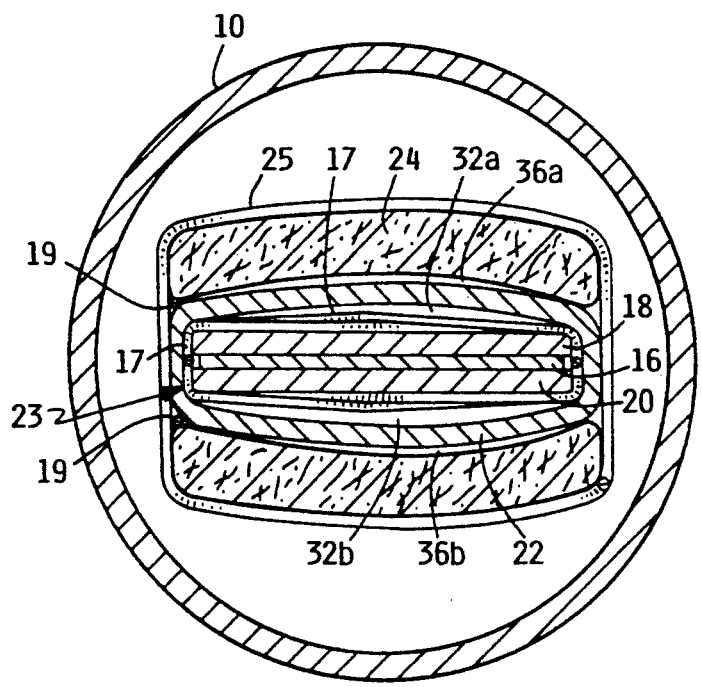
FIG. 2 shows a view taken along the lines 2—2 of FIG. 1.
Figure 5:
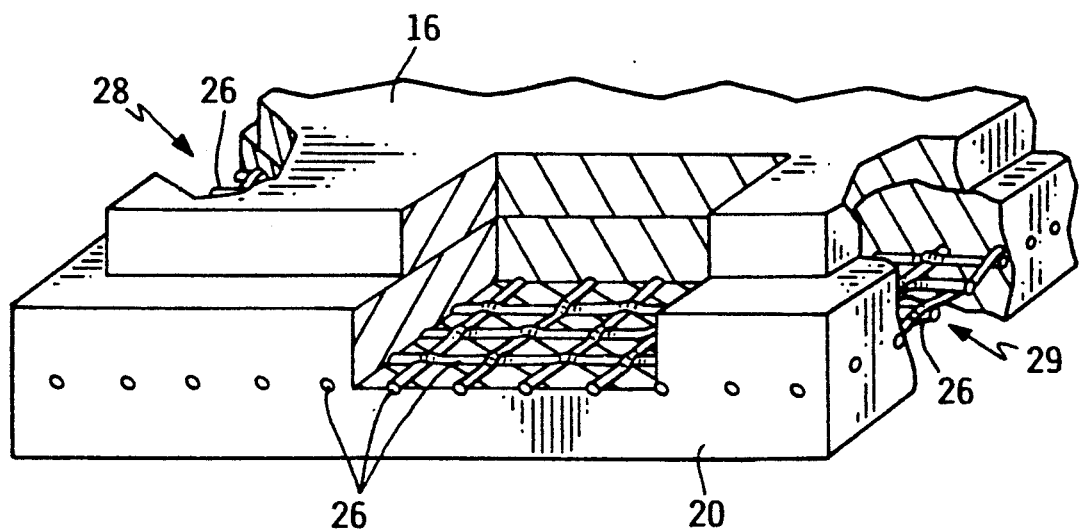
FIG. 5 shows an exploded isometric view of the anode material in a prior art device.

FIG. 2 illustrates some of the problems with prior art devices. The anode materials 18, 20 are applied against the surfaces of the blade 16, and a wire wrap 17 is tightly applied about the entire subassembly over the length of the blade 16. The anode materials 18, 20 are either equal in width or slightly wider than blade 16. The tight wrapping of the anode materials about blade 16 by wire 17, results in wire 17 biting into the edge corners of anode materials 18, 20. This produces roughened edge portions, as are shown in FIG. 5, which can contribute to short circuiting of the active elements. FIG. 5 illustrates the construction of an anode material 20 in facing relationship with blade 16, according to the prior art. Anode material 20 is preferably formed of a cadmium mixture which is impregnated into and around a nickel wire screen 26. If the anode material 20 is made with a surface equal to or wider than blade 16, and then wire 17 is tightly wound around the entire assembly, wire 17 will cause the anode material to degrade at respective crossing points 28, 29, as illustrated in FIG. 5. This causes some of the anode material to deform or fall away and exposes the wire ends of the interior screen 26. The exposed wire ends are typically relatively short sections of nickel wire with sharp points, and it is relatively easy for these sharpened ends to penetrate through insulator 22 during subsequent assembly steps. If any of the wire ends of screen 26 penetrate through insulator 22 and come into contact with cathode 24, there is created an electrical short circuit between the anode and cathode, and the performance of the oxygen sensor is degraded or, in some cases, destroyed. It is possible to deal with this problem by using protector inserts between the anode and cathode, preferably along the edges where the material degradation is likely to occur. These protectors could take the form of plastic edge guards which overlay the edges of the anode, or of the insulator, to electrically isolate any potential conductive paths between the anode and cathode. However, the use of such protector inserts does reduce the overall contact surface area between the anode and cathode, and also introduces additional constructional elements which must be used during assembly.

Figure 3:
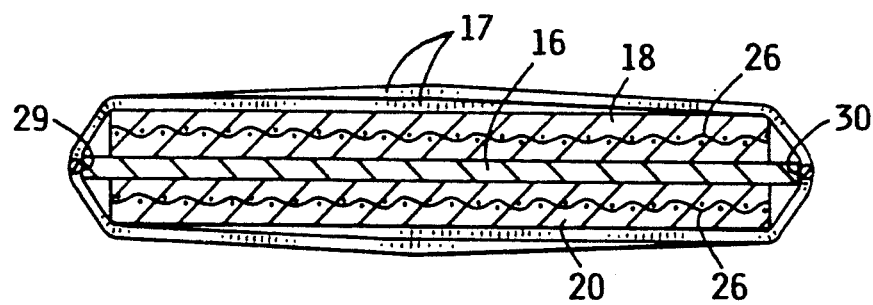
FIG. 3 shows a cross-section view of one feature of the present invention.
Figure 4:
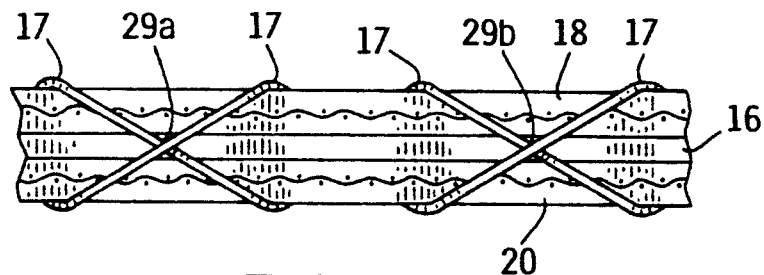
FIG. 4 shows a side view of FIG. 3.

FIG. 3 illustrates a cross-sectional view of one feature of the invention which tends to overcome this problem. In this example, blade 16 is constructed to be wider than either anode material 18 or anode material 20. When wire 17 is now tightly wound about the assembly the principal contact point for wire 17 is against the outer edge 29 of blade 16 and the opposite outer edge 30 of blade 16. This relieves the biting force into anode elements 18, 20, and thereby reduces the amount of damage to the anode elements. This reduces the likelihood of exposure of any of the fine wire ends of screen 26. FIG. 4 illustrates a partial side view of the construction of FIG. 3, to show two representative wire crossing points 29a, 29b, each of which crosses at the edge of blade 16.

A further problem with the prior art is illustrated in FIG. 2, with respect to the voids which inherently exist between the active elements of the sensor. Because of the prior art wrapping techniques, insulator 22 becomes wrapped about the interior anode elements by virtue of wrapping wire 19, but the principal force of the wrapping wire is against the corners of insulator 22. This provides very little inward force across the center surface area of insulator 22, thereby tending to create a void 32a along the upper surface of the anode 23 and a void 32b along the lower surface of the anode 23. These voids can reduce the effective contact area of the electrolyte with respect to the anode, and can cause degraded performance of the oxygen sensor. Similarly, the cathode 24 is wrapped by a nylon thread 25 about insulator 22 and the other interior components. The primary force of this wrapping is also directed against the corners of cathode 24, and to some extent across the line contact of the nylon thread as it bridges over the wider surface area. However, the cathode 24 is typically made from soft, spongy material, and therefore a plurality of voids 36a, 36b may be formed between portions of the cathode 24 and the insulator 22. These voids also reduce the electrolyte contact area and can seriously degrade the performance of the oxygen sensor.

Figure 6:
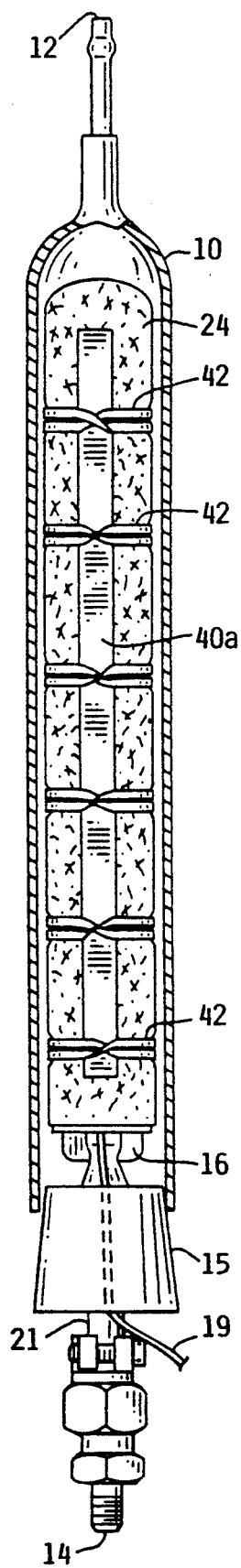
FIG. 6 shows a front elevation view of the present invention.
Figure 7:
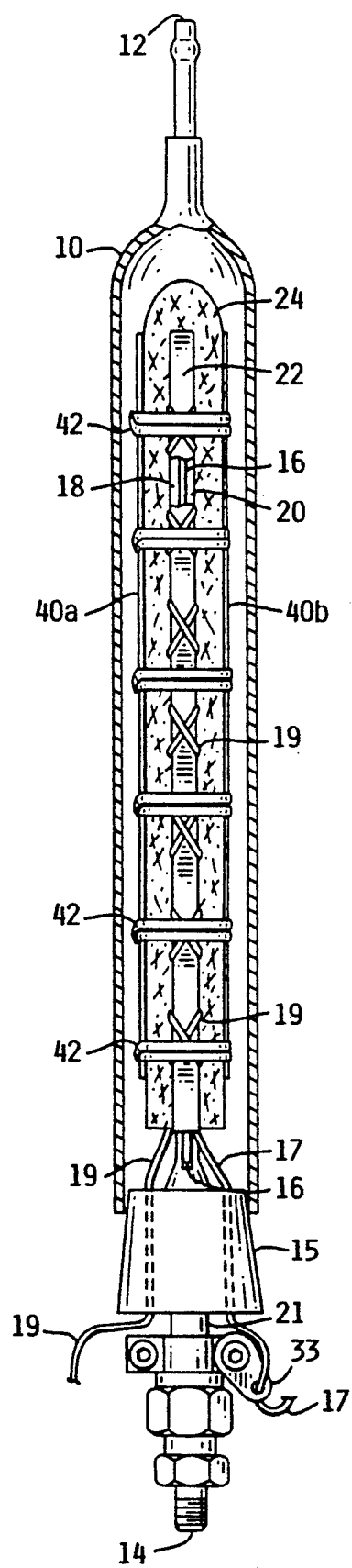
FIG. 7 shows a side elevation view of the present invention.

FIGS. 6 and 7 illustrate another feature of the invention which is directed to reducing the contact surface area voids which have occurred in the prior art construction. FIG. 6 shows a front elevation view of the interior oxygen sensor components, and FIG. 7 shows a right side elevation view of the same. The cathode material 24 is overlaid over the active components interior of the sensor, and support struts 40a, 40b are overlaid along the length of cathode 24. Support struts 40a, 40b are compressed inwardly against cathode 24 by a plurality of elastic bands 42. Elastic bands 42 are stretched so as to provide a relatively uniform inwardly-directed force, and this force is applied against support struts 40a, 40b to provide a uniform inwardly-directed force along virtually the entire length of the oxygen sensor active elements, along the centerline. The inwardly-directed force provided by this construction compresses cathode 24 uniformly inwardly along its length, and also compresses insulator 22 uniformly inward along its length. Therefore, the internal voids which have existed in prior art constructions are eliminated, by the relatively constant, uniform, inward force directed along the length of the active elements of the sensor. Support struts 40a, 40b may be made from plastic or other materials which are impervious to the chemical reactions which occur inside of the envelope 10, and the elastic bands 42 may be made from rubber or other materials which are impervious to the same chemicals.

An alternative form of construction which has some utility is to utilize the construction of FIGS. 6 and 7, but instead of utilizing elastic bands 42 to exert an inward force against the cathode 24, the wire 19 could be wrapped about the exterior of cathode 24 and support struts 40a, 40b. In this construction, wire 19 becomes not only the conductive path making contact with cathode 24, but also serves as the wrapping assembly to secure cathode 24 in close contact against the inner components.

FIGS. 6 and 7 also illustrate a further improvement in electrical construction. The internal anode wire 17 is positively connected to a grounding bracket clamped against tube 21. This connection eliminates stray currents and assures a positive circuit ground connection to the anode.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed is:

1. A method of constructing an oxygen sensor in a layered construction, comprising the steps of:
   a) overlaying a flat metallic blade with a sheet of anodic material against each flat surface of said blade, with said anodic sheets being narrower than said blade;
   b) wrapping a first wire about said sheets and said blade, contacting the respective edges of said blade with each wrap;
   c) overlaying said wrapped sheets and blade with a porous insulator material, and wrapping a second wire about said insulator;
   d) overlaying said porous insulator with a porous cathode material;
   e) applying an elongated strut against said porous cathode material on each of two sides in approximate alignment with the center of said flat metallic blade; and
   f) applying a plurality of elastic bands about said elongated struts and said porous cathode material, whereby a uniform inwardly-directed force is applied along the elongate length of said cathode material.

2. The method of claim 1, further comprising impregnating said porous insulator material with an electrolyte solution.

3. The method of claim 2, wherein said electrolyte solution further comprises potassium hydroxide.

4. The method of claim 2, further comprising inserting said layered construction in an envelope which is impervious to oxygen.

5. The method of claim 1, wherein the step of wrapping said first wire further comprises wrapping said first wire in criss-cross fashion about said sheets and said blade.

6. The method of claim 5, wherein said first wire is wrapped to cross along the respective edges of said blade.

7. The method of claim 6, further comprising electrically connecting said first wire to said blade.

* * * * *